(12) United States Patent
Schütz et al.

(10) Patent No.: US 11,573,281 B2
(45) Date of Patent: Feb. 7, 2023

(54) MAGNETIC RESONANCE FINGERPRINTING METHOD FOR RECORDINGS WITH A CONTRAST AGENT

(71) Applicant: Bayer Aktiengesellschaft, Leverkusen (DE)

(72) Inventors: Gunnar Schütz, Berlin (DE); Gregor Jost, Berlin (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 17/287,464

(22) PCT Filed: Oct. 18, 2019

(86) PCT No.: PCT/EP2019/078387
§ 371 (c)(1),
(2) Date: Apr. 21, 2021

(87) PCT Pub. No.: WO2020/083778
PCT Pub. Date: Apr. 30, 2020

(65) Prior Publication Data
US 2021/0389402 A1 Dec. 16, 2021

(30) Foreign Application Priority Data
Oct. 25, 2018 (EP) .................................... 18202461

(51) Int. Cl.
*G01R 33/56* (2006.01)
*A61B 5/055* (2006.01)
*A61B 5/00* (2006.01)

(52) U.S. Cl.
CPC .......... *G01R 33/5601* (2013.01); *A61B 5/055* (2013.01); *A61B 5/4244* (2013.01); *G01R 33/5608* (2013.01); *A61B 2576/02* (2013.01)

(58) Field of Classification Search
USPC ....................................................... 324/309
See application file for complete search history.

(56) References Cited

U.S. PATENT DOCUMENTS

| 6,039,931 A | 3/2000 | Schmitt-Willich et al. |
| 2009/0155181 A1* | 6/2009 | Rowe ................... A61K 49/189 424/9.3 |

(Continued)

FOREIGN PATENT DOCUMENTS

WO    2018187760 A1    10/2018

OTHER PUBLICATIONS

Anderson, C.E., et al. (2017). "Dual Contrast—Magnetic Resonance Fingerprinting (DC-MRF): a Platform for Simultaneous Quantification of Multiple MRI Contrast Agents," Scientific Reports, 7(8431): 1-10.

(Continued)

*Primary Examiner* — Rodney E Fuller
(74) *Attorney, Agent, or Firm* — Morrison & Foerster LLP

(57) ABSTRACT

Systems, methods, and computer program products for determining different states of a contrast agent in different types of tissue can involve generating a magnetic resonance waveform for the contrast agent in an examination region that includes multiple tissue types. The contrast agent may have different relaxation-shortening effects in each different tissue type. The generated waveform may be compared to database waveforms to determine the concentration of the contrast agent in each tissue type in the examination region.

19 Claims, 4 Drawing Sheets

(56) References Cited

U.S. PATENT DOCUMENTS

| | | | | |
|---|---|---|---|---|
| 2009/0264733 | A1* | 10/2009 | Corum | G01R 33/561 600/420 |
| 2011/0275928 | A1* | 11/2011 | Kim | A61B 5/055 600/420 |
| 2012/0101367 | A1* | 4/2012 | Kim | G01R 33/5602 600/420 |
| 2014/0142417 | A1* | 5/2014 | Reeder | A61B 5/055 600/420 |
| 2018/0146880 | A1* | 5/2018 | Cao | A61B 5/4244 |
| 2019/0055556 | A1* | 2/2019 | Monje-Deisseroth | A61K 31/7105 |
| 2019/0246938 | A1* | 8/2019 | Gharagouzloo | G01R 33/5635 |
| 2020/0041595 | A1* | 2/2020 | Flask | G06T 7/0016 |
| 2021/0298662 | A1* | 9/2021 | Gharagouzloo | A61K 31/445 |

OTHER PUBLICATIONS

Cauley, S.F. et al. (2015). "Fast Group Matching for MR Fingerprinting Reconstruction," Magnetic Resonance in Medicine, 74:523-528.

Clement, O. et al. (1992). "Gadolinium-Ethoxybenzyl-DTPA, a New Liver-Specific Magnetic Resonance Contrast Agent," Investigative Radiology, 27:612-619.

Cloos, M.A. et al. (2016) "Online Radial Multiband Magnetic Resonance Fingerprinting," Center for Advanced Imaging Innovation and Research, a NIBIB Biomedical Technology Resource Center, 1-5.

International Search Report dated Jan. 24, 2020, for PCT Patent Application No. PCT/EP2019/078387 filed Oct. 18, 2019, 3 pages.

Jiang, Y. et al. (2015). "MR Fingerprinting Using Fast Imaging with Steady State Precession (FISP) with Spiral Readout," Magn Reson Med. 74(6):1621-1631.

Kaggie, J. et al. (2018). "T1 and T2 1,10-12 Mapping of Delayed Gadolinium Enhancement in Osteoarthritis with MR Fingerprinting", Proceedings of the International Society for Magnetic Resonance in Medicine, ISMRM, 20th Annual Meeting and Exhibition, Melbourne, Australia, May 5-11, 2012, Nr. 1435.

Karaosmanoglu A.D. et al. (2016). "Magnetic, Resonance Imaging of Liver Metastasis," Seminars in Ultrasound CT and MRI, 37(6):533-548.

Ma, D. et al. (2013). "Magnetic Resonance Fingerprinting," Nature, 495:187-193.

Mehta, B.B. et al. (2018). "Magnetic Resonance Fingerprinting: a Technical Review: Magnetic Resonance in Medicine," Magnetic Resonance in Medicine, 81(1):25-46.

Rohrer, M. et al. (2005). "Comparison of Magnetic Properties of MRI Contrast Media Solutions at Different Magnetic Field Strengths," Investigative Radiology, 40(11):715-724.

Schuhmann-Giampieri, G. et al. (1992). "Preclinical Evaluation of Gd-EOB-DTPA as a Contrast Agent in MR Imaging of the Hepatobiliary System," Radiology, 183:59-64.

Unal, E. et al. (2017). "Multiparametric orpractical quantitative liver MRI: towards millisecond, fat fraction, kilopascal and function era," Expert Review of Gastroenterology and Nepatology, 11(2):167-182.

Xie, J. et al. (2017). "Fast Dictionary Generation and Searching for Magnetic Resonance Fingerprinting," Annu Int Conf IEEE Eng Med Biol Soc., 3256-3259.

* cited by examiner

MAGNETIC RESONANCE FINGERPRINTING METHOD FOR RECORDINGS WITH A CONTRAST AGENT

CROSS REFERENCE TO RELATED APPLICATIONS

This application is a national stage application under 35 U.S.C. § 371 of International Application No. PCT/EP2019/078387, filed internationally on Oct. 18, 2019, which claims the benefit of European Application No. 18202461.2, filed Oct. 25, 2018.

FIELD OF THE DISCLOSURE

The present invention relates to the technical field of magnetic resonance imaging. The present invention provides a process, a system, and a computer program product for determining different states of a contrast agent in different tissue types in a magnetic resonance fingerprinting method.

BACKGROUND

Magnetic resonance imaging, MRI for short, is an imaging method that is used especially in medical diagnostics for depicting structure and function of tissue and organs in the human or animal body.

In MRI, the magnetic moments of protons in an examination object are aligned in a basic magnetic field, with the result that there is a macroscopic magnetization along a longitudinal direction. This is then deflected from the resting position by irradiation with high-frequency (HF) pulses (excitation). The return of the excited states to the resting position (relaxation), or magnetization dynamics, is then detected as relaxation signals by means of one or more HF receiver coils.

For spatial encoding, rapidly switched magnetic gradient fields are superimposed on the basic magnetic field. The acquired relaxation signals, or detected and spatially resolved MRI data, are initially present as raw data in a spatial frequency domain, and can be transformed by subsequent Fourier transformation into the spatial domain (image space).

In the case of native MRI, the tissue contrasts are created by the different relaxation times (T1 and T2) and the proton density.

T1 relaxation describes the transition of the longitudinal magnetization to its equilibrium state, T1 being the time taken to reach 63.21% of the equilibrium magnetization prior to the resonance excitation. It is also called longitudinal relaxation time or spin-lattice relaxation time.

T2 relaxation describes in analogous manner the transition of transverse magnetization to its equilibrium state.

MRI contrast agents exert their effect by altering the relaxation times of structures that take up contrast agents. A distinction can be made between two groups of substances: paramagnetic and superparamagnetic substances. Both groups of substances have unpaired electrons that induce a magnetic field around the individual atoms or molecules.

Superparamagnetic contrast agents result in a predominant shortening of T2, whereas paramagnetic contrast agents mainly lead to a shortening of T1.

The effect of said contrast agents is indirect, since the contrast agent itself does not emit a signal, but instead merely influences the intensity of signals in its vicinity.

An example of a superparamagnetic contrast agent is iron oxide nanoparticles (SPIO, superparamagnetic iron oxide).

Examples of paramagnetic contrast agents are gadolinium chelates such as gadopentetate dimeglumine (trade name: Magnevist® and others), gadoteric acid (Dotarem®, Dotagita®, Cyclolux®), gadodiamide (Omniscan®), gadoteridol (ProHance®), and gadobutrol (Gadovist®).

Characteristic features of contrast agents based on gadoxetic acid are specific uptake by liver cells (hepatocytes), accumulation in the functional tissue (parenchyma), and enhancement of contrasts in healthy liver tissue. The cells of cysts, metastases, and most hepatocellular carcinomas no longer function in the same way as normal liver cells, show little or no uptake of contrast agent, are not depicted with enhancement, and are identifiable and localizable as a result. Examples of contrast agents based on gadoxetic acid are described in U.S. Pat. No. 6,039,931A; they are commercially available for example under the trade names Primovist® or Eovist®.

The contrast-enhancing effect of Primovist®/Eovist® is mediated by the stable gadolinium complex Gd-EOB-DTPA (gadolinium ethoxybenzyl diethylenetriaminepentaacetic acid). DTPA forms with the paramagnetic gadolinium ion a complex that has extremely high thermodynamic stability. The ethoxybenzyl (EOB) radical is the mediator of the hepatobiliary uptake of the contrast agent. In this process, hepatobiliary uptake is mediated by an organic anion transport system that is also involved in the uptake of bilirubin into liver cells (O. Clément et al., *Gadolinium-ethoxybenzyl-DTPA, a new liver-specific magnetic resonance contrast agent. Kinetic and enhancement patterns in normal and cholestatic rats*; Invest Radiol (1992); 27: 612-619).

SUMMARY OF THE DISCLOSURE

Using magnetic resonance fingerprinting methods, it is possible to generate more detailed images of an examination object in a shorter time. Magnetic resonance fingerprinting methods are described for example in Ma et al., *Magnetic Resonance Fingerprinting, Nature,* 495: 187-192 (2013); Jiang et al., *MR Fingerprinting Using Fast Imaging with Steady State Precession (FISP) with Spiral Readout*, Magnetic Resonance in Medicine 74: 1621-1631 (2015) or Cloos et al., *Online Radial Multiband Magnetic Resonance Fingerprinting*, ISMRM 2016: 608.

A magnetic resonance fingerprinting method is a quantitative measurement method in which a plurality of magnetic resonance images of an examination object is initially generated with varying acquisition parameters. In this method, the acquisition parameters are usually varied in a pseudo-randomized manner. A position-dependent magnetic resonance waveform is then generated for the individual pixels (voxels) of the magnetic resonance images. The waveform that is determined is then compared for each voxel with a plurality of waveforms saved in a database, each of the waveforms in the database being matched to a specific value of at least one tissue parameter. The database waveforms represent expected waveforms and are predetermined and/or precalculated. A volume element of a sample in which the value of the at least one tissue parameter corresponds to the specific database value should exhibit the waveform saved in the database in a magnetic resonance measurement. Thus, if a matching waveform is identified, the associated value of the at least one tissue parameter can be read from the database.

This allows the spatial distribution of tissue-specific parameters (such as the transverse relaxation T2 or the longitudinal relaxation T1; so-called T1 and T2 maps) in the imaged examination object to be quantitatively determined from measured MR data. An advantage of the magnetic resonance fingerprinting method is that a plurality of tissue parameters can be acquired simultaneously in a single measurement.

C.E. Anderson et al. report on the simultaneous measurement of tissue parameters for two contrast agents administered simultaneously (*Dual Contrast—Magnetic Resonance Fingerprinting* (*DCMRF*): *A Platform for Simultaneous Quantification of Multiple MRI Contrast Agents*; Scientific Reports 7; 8431: 1-10; DOI:10.1038/s41598-017-08762-9). The method exploits the fact that the contrast agents used differ in their relaxivities and can therefore be differentiated.

When a contrast agent is administered, it is distributed throughout the body. The contrast agent, which may be present in areas of different tissue, brings about a measured change in relaxation. The signals can here originate from different tissue types (e.g. functional tissue (parenchyma), interstitial tissue (interstitium), and/or a tissue fluid (e.g. blood, lymph, bile).

What is being sought is a solution with which it is possible to distinguish different tissue types present in a volume element in a single measurement with just one contrast agent.

According to some embodiments, the present invention firstly provides a method comprising the following steps:
providing a magnetic resonance fingerprint database,
  wherein the magnetic resonance fingerprint database comprises database waveforms for a specific contrast agent in at least two different tissue types, a first tissue type and a second tissue type,
  wherein the contrast agent has a different state in the first tissue type than in the second tissue type,
acquiring a magnetic resonance waveform for a volume element of an examination region by means of a magnetic resonance fingerprinting method using the contrast agent,
comparing the magnetic resonance waveform with database waveforms,
identifying a database waveform having a defined correspondence with the magnetic resonance waveform,
determining the states of the contrast agent in the volume element,
outputting information on the states of the contrast agent in the volume element.

According to some embodiments, the present invention further provides a system comprising
a receiving unit,
a control unit,
a signal comparison unit, and
an output unit,
  wherein the control unit is configured to cause the receiving unit to receive a magnetic resonance waveform for at least one volume element of the examination region, the magnetic resonance waveform having been generated in a magnetic fingerprinting method using a contrast agent,
  wherein the control unit is configured to cause the receiving unit to receive a plurality of database waveforms from a magnetic resonance fingerprint database, each waveform being matched to at least two database values of two tissue parameters, a first tissue parameter and a second tissue parameter, wherein the first tissue parameters characterizes a first state of the contrast agent in a first tissue type and the second tissue parameter characterizes a second state of the contrast agent in a second tissue type,
  wherein the control unit is configured to cause the signal comparison unit to compare the magnetic resonance waveform with the database waveforms, to identify a database waveform having a defined correspondence, and to determine the at least two database values matched to the identified database waveform,
  wherein the control unit is configured to cause the output unit to save and/or output the at least two database values or values derived from the at least two database values.

According to some embodiments, the present invention further provides a computer program product comprising a computer program that can be loaded into a memory of a computer, where it causes the computer to execute the following steps:
receiving a magnetic resonance waveform for a volume element of an examination region from a magnetic resonance fingerprinting method using a contrast agent,
receiving database waveforms, each database waveform being matched to different states of the contrast agent in different tissue types,
comparing the magnetic resonance waveform with database waveforms,
identifying a database waveform having a defined correspondence with the magnetic resonance waveform,
determining the different states of the contrast agent in the volume element,
outputting information on the different states of the contrast agent in the volume element.

According to some embodiments, the invention further provides for the use of a contrast agent in a magnetic resonance fingerprinting method, wherein the contrast agent has different states in at least two different tissue types, for determining the different states in an imaged volume element.

According to some embodiments, the invention further provides a contrast agent for use in a magnetic resonance fingerprinting method, wherein the contrast agent has different states in at least two different tissue types, the different states in an imaged volume element being recorded simultaneously in one measurement.

The invention is elucidated in detail herein below without making a distinction between the subjects of the invention (method, system, computer program product, use, contrast agent to be used). Rather, the elucidations that follow are intended to apply by analogy to all subjects of the invention, irrespective of the context (method, system, computer program product, use, contrast agent to be used) in which they occur.

Where steps in a sequence are mentioned in the present description or in the claims, this does not necessarily mean that the invention is limited to the sequence mentioned. Rather, it is also possible for the steps to be executed in a different sequence or in parallel to one another, unless one step builds on another step, in which case the step building on the previous step must by definition be executed thereafter (which will however become clear in the individual case). The sequences mentioned are thus preferred embodiments of the invention.

According to some embodiments, the present invention uses a magnetic resonance fingerprinting method in order to simultaneously record different states of a contrast agent in different tissue types in one measurement.

A tissue type is understood as meaning an assemblage of differentiated cells including their extracellular matrix. Examples of tissue types are epithelial tissue, connective and supporting tissue (bone tissue, cartilage tissue, adipose tissue), muscle tissue, nerve tissue, and liver tissue. Tissue fluids or liquid tissue (e.g. blood, lymph, bile) are also regarded as tissue types here. It is also possible for diseased and healthy tissue to represent two different tissue types.

A contrast agent is understood as meaning a substance or substance mixture, the presence of which in a magnetic resonance measurement results in an altered signal. The contrast agent preferably leads to a shortening of the T1 time and/or of the T2 time.

The contrast agent is present in different states in at least two tissue types. This means there is a first tissue type and a second tissue type. Contrast agent administered to an examination object is distributed in the tissue types; administered contrast agent is accordingly present both in the first and in the second tissue type. How the contrast agent is distributed in the tissue types can in principle be determined experimentally and for example expressed by a partition coefficient. A partition coefficient of this kind can for example be the ratio of the concentration of the contrast agent in the first tissue type and the concentration of the contrast agent in the second tissue type. It is possible for the partition coefficient to itself be concentration-dependent, that is to say it can change with the concentration of the contrast agent in a tissue type.

The contrast agent has a different state in the first tissue type than in the second tissue type. A different state results in altered relaxation. A state can be characterized by at least one value of a tissue parameter. In one embodiment, the terms "another state" or "different states" mean that the molar T1 relaxivity of the contrast agent in the first tissue type is different than in the second tissue type. In another embodiment, the terms "another state" or "different states" mean that the molar T2 relaxivity of the contrast agent in the first tissue type is different than in the second tissue type. In a further embodiment, the terms "another state" or "different states" mean that both the molar T1 relaxivity and molar T2 relaxivity of the contrast agent in the first tissue type are different than in the second tissue type.

The molar relaxivity is a customary measure of the effectiveness, i.e. relaxation-shortening effect, of a contrast agent. Its unit can be expressed in $(s \cdot mol/L)^{-1}$ (seconds× mol/liters)$^{-1}$.

The molar relaxivity in the first tissue type is preferably at least 1.5 times greater than in the second tissue type, more preferably at least 2 times greater, even more preferably at least 2.5 times greater. In a particularly preferred embodiment, the molar relaxivities in the two different tissue types differ by a factor of at least 1.5 (preferably at least 2, even more preferably at least 2.5) at a magnetic field strength of the basic magnetic field of at least 1.5 tesla, preferably of at least 2 tesla, even more preferably of at least 2.5 tesla, even more preferably of at least 3 tesla, most preferably at a magnetic field strength of 0.4 tesla to at least 3 tesla.

In a particularly preferred embodiment, the contrast agent is a substance or a substance mixture having gadoxetic acid or a salt of gadoxetic acid as contrast-enhancing active substance. Very particular preference is given to the disodium salt of gadoxetic acid (Gd-EOB-DTPA disodium). Gd-EOB-DTPA has a significantly higher molar relaxivity in liver cells (hepatocytes) than it has for example in plasma, and a significantly higher molar relaxivity in plasma than in bile.

Table 1 shows the molar relaxivities (in $(s \cdot mmol/L)^{-1}$) of Gd-EOB-DTPA in different tissue types at different magnetic field strengths of the basic magnetic field.

TABLE 1

|  | 0.47 T | 1.41 T | 1.5 T | 3 T |
|---|---|---|---|---|
| Water | 5.3[1] |  | 4.7[1] | 4.3[1] |
| Bile |  | 5.6 ± 0.3 | 5.6 ± 0.4 | 5.6 ± 0.3 |
| Urine |  | 5.5 ± 0.1 | 5.5 ± 0.2 | 5.6 ± 0.1 |
| Plasma | 8.7[1] |  | 6.9[1] | 6.2[1] |
| Blood | 11.0[2] | 8.1 ± 0.2 | 7.3[1]/8.3 ± 0.3 | 7.2 ± 0.1 |
| Liver tissue | 16.6[2] | 14.0 ± 2.8 | 16.4 ± 3.1 | 13.4 ± 4.0 |

[1]Rohrer et al. Radiol 2005; 40(11): 715-724
[2]Schuhmann-Giampieri et al. Radiol. 1992; 183: 59-64

The high molar relaxivity in liver tissue is surprisingly maintained even at high (clinically relevant) magnetic field strengths.

The invention makes it possible to distinguish contrast agent present in the first tissue type from contrast agent present in the second tissue type, even when both tissue types are present in the same volume element that is imaged as a voxel in magnetic resonance image data.

The "examination object" is usually a living being, preferably a mammal, very particularly preferably a human. The examination region is part of the examination object, for example an organ such as the liver or part of an organ.

The examination region, also called the field of view (FOV), represents in particular a volume that is imaged in the acquired magnetic resonance image data. The examination region is typically defined by a user, for example on an overview image (localizer). It is of course also possible for the examination region to alternatively or additionally be defined automatically, for example on the basis of a selected protocol.

A contrast agent that undergoes distribution in the examination region is administered to the examination object. The examination region is introduced into a basic magnetic field The examination region is subjected to a magnetic resonance fingerprinting method and a magnetic resonance waveform is determined for at least one volume element of the examination region (for details see FIG. 2 and the associated description).

The magnetic resonance fingerprinting method typically provides for acquisition of a magnetic resonance waveform for a plurality of voxels by means of a pseudorandomized or incoherent acquisition scheme. It is also possible for the magnetic resonance waveform to be acquired from a region that has coarser resolution than one voxel. In such instances, the magnetic resonance waveform can for example be acquired as an average over a plurality of voxels.

The magnetic resonance fingerprinting method includes, in particular, the setting of different acquisition parameters for the acquisition of different magnetic resonance signals. The acquisition parameters can here be varied in a pseudo-randomized or incoherent manner. Examples of acquisition parameters that may be changed in the acquisition of the magnetic resonance waveform include an echo time, formation and/or number of high-frequency pulses, formation and/or number of gradient pulses, diffusion encoding, etc. This allows the acquisition with the magnetic resonance fingerprinting method of a magnetic resonance waveform characteristic of the voxel, a so-called fingerprint of the voxel.

In a further step of the method according to the invention, the magnetic resonance waveforms are compared with waveforms saved in a magnetic resonance fingerprint database (database waveforms).

The database waveforms may be determined, for example in a calibration measurement, and/or simulated. Methods for generating database waveforms are described in the prior art (see for example J. Xie et al.: *Fast dictionary generation and searching for magnetic resonance fingerprinting*, Conf Proc IEEE Eng Med Biol Soc. 2017 July; 2017:3256-3259. doi: 10.1109/EMBC.2017.8037551).

The magnetic resonance fingerprinting method typically provides for the assignment of a database waveform to the acquired magnetic resonance waveform based on the result of the signal comparison. The signal comparison can include a determination of similarity between the acquired magnetic resonance waveform and the plurality of database waveforms, wherein the database waveform that shows the greatest similarity to the magnetic resonance waveform is matched to the magnetic resonance waveform.

It is also possible for a similarity threshold to be defined that must be reached in order to make a match.

Methods for comparing and identifying similarities are described in the prior art (see for example S.F. Cauley et al., *Fast group matching for MR fingerprinting reconstruction*, Magnetic Resonance in Medicine 74:523-528 (2015)).

Matched to the different database waveforms are database values of tissue parameters specific in each case.

The database values associated with the matched database waveform can then for example be set as measured values of tissue parameters of the examined volume element. As the result of the signal comparison, the measured values of the tissue parameters for the corresponding voxel obtained using the magnetic resonance fingerprinting method can for example be outputted or saved.

A selection of possible tissue parameters that can be quantified using the magnetic resonance fingerprinting method includes: a T1 relaxation time, a T2 relaxation time, a diffusion value (for example an apparent diffusion coefficient, ADC), a magnetization moment, a proton density, a resonance frequency, a concentration of a substance, etc. Other tissue parameters deemed appropriate by those skilled in the art are of course also possible.

According to some embodiments of the invention, the database values/measured values of the tissue parameters are associated with the different states of the employed contrast agent in the at least two different tissue types.

When two different tissue types are present in an examined volume element and a magnetic resonance waveform is being acquired for the volume element after administration of a contrast agent, it is possible, through identification of the associated database waveform, for example to determine the T1 relaxation time and T2 relaxation time of the contrast agent simultaneously for both tissue types as associated database values and to calculate therefrom, for example, the concentration of the contrast agent in the first tissue type and the concentration time of the contrast agent in the second tissue type for the corresponding volume element.

The database values determined and/or values derived from the database values can be saved and/or outputted. A derived value is usually a value arising from a calculation based on the database value. An example of a derived value is the concentration of the contrast agent in a tissue type.

According to some embodiments, the present invention provides a system with which it possible to execute the method according to the invention.

The system comprises a receiving unit, a control unit, a signal comparison unit, and an output unit. It is possible for the mentioned units to be components of a single computer system, but it is also possible for the mentioned units to be components of a plurality of separate computer systems that are connected to one another via a network in order to transmit data and/or control signals from one unit to another unit.

A "computer system" is a system for electronic data processing that processes data by means of programmable computation rules. Such a system typically comprises a "computer", i.e. unit comprising a processor for the execution of logic operations, and also peripherals.

In computer technology, "peripherals" refers to all devices that are connected to the computer and are used for control of the computer and/or as input and output devices. Examples thereof are monitor (display), printer, scanner, mouse, keyboard, drives, camera, microphone, speakers, etc. Internal ports and expansion cards are also regarded as peripherals in computer technology.

Today's computer systems are commonly subdivided into desktop PCs, portable PCs, laptops, notebooks, netbooks and tablet PCs, and so-called handhelds (e.g. smartphones); all such systems can be used for execution of the invention.

Inputs into the computer system are made via input devices, for example a keyboard, a mouse, a microphone, and/or the like. "Input" is also to be understood as meaning the selection of an entry from a virtual menu or from a virtual list or clicking on a checkbox and the like.

The system according to some embodiments of the invention is configured to receive at least one magnetic resonance waveform and a plurality of database waveforms, to compare the at least one magnetic resonance waveform with the database waveforms, as the result of the comparison to identify a database waveform having a defined correspondence with the magnetic resonance waveform, to determine at least two database values matched to the identified database waveform, and to save and/or output the database values determined or values derived from the database values determined.

The control unit is used to control the receiving unit, the signal comparison unit, and the output unit and to coordinate the flow of data and signals between different units. It is possible for there to be a plurality of control units.

The receiving unit is used to receive the at least one magnetic resonance waveform. The at least one magnetic resonance waveform may be transmitted for example by a magnetic resonance system or read from a data storage device. The magnetic resonance system may be a component of the system according to the invention. However, it is also possible for the system according to the invention to be a component of a magnetic resonance system.

The receiving unit is also used to receive a plurality of database waveforms from a magnetic resonance fingerprinting database. The magnetic resonance fingerprinting database may be a component of the system according to the invention. Saved in the magnetic resonance fingerprinting database is a large number of database waveforms. To each database waveform are matched specific values (database values) of tissue parameters. The database waveforms indicate the waveform to be expected for a sample that has corresponding values of the tissue parameters. Some of the database waveforms indicate the waveforms to be expected for a sample in which at least two different tissue types are present in a volume element and an administered contrast agent has different states in the at least two tissue types. One state is characterized by a specific value (database value) of a first tissue parameter, the other state by a specific value (database value) of a second tissue parameter.

The at least one magnetic resonance waveform and the plurality of database waveforms are transmitted from the receiving unit to the signal comparison unit.

The signal comparison unit is configured to compare the at least one magnetic resonance waveform with different database waveforms in order to identify a database waveform having a defined correspondence with the magnetic resonance waveform. Once the database waveform has been identified, the database values matched to the database waveform are determined.

The output unit is configured to save and/or output the database values determined. These are usually saved in a data storage device that is part of the system according to the invention or is connected to it via a network. Output is usually onscreen. It is possible for the output to take the form of a two- or three-dimensional image. It is possible for the image to depict the examined examination region and a color and/or gray tone to be selected for individual volume elements on the basis of one or more database values determined for the volume element.

It is possible for derived values to be calculated on the basis of the database values determined. The calculation can be performed for example by the control unit and/or the signal comparison unit.

BRIEF DESCRIPTION OF THE DRAWINGS

The invention is elucidated in detail herein below with reference to figures, without any intention to restrict the invention to the features or combinations of features shown in the figures.

In the figures below.

DETAILED DESCRIPTION OF EXEMPLARY EMBODIMENTS

Figure 1:
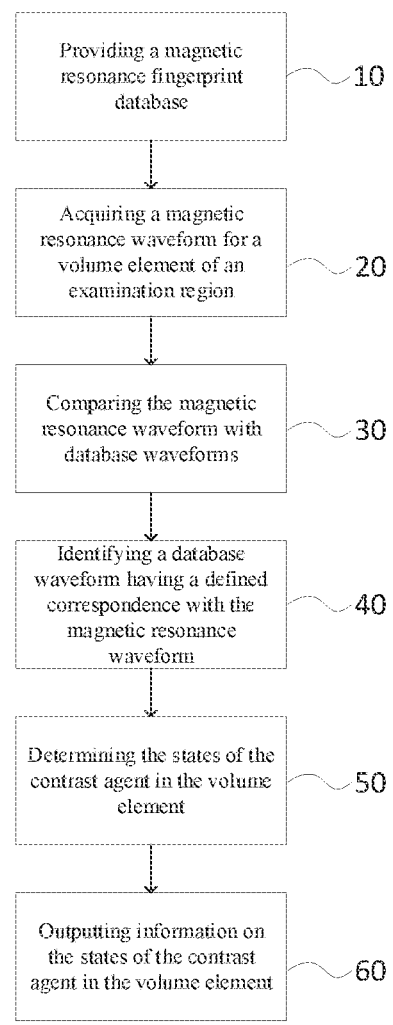
FIG. 1 shows an exemplary flowchart describing a method according to some embodiments in the form of a sequence of successive steps.

FIG. 1 shows an exemplary schematic representation of the course of the method according to some embodiments of the invention in the form of a sequence of successive steps. The sequence comprises the steps of
providing a magnetic resonance fingerprint database (10)
acquiring a magnetic resonance waveform for a volume element of an examination region by means of a magnetic resonance fingerprinting method using a contrast agent (20)
comparing the magnetic resonance waveform with database waveforms (30)
identifying a database waveform having a defined correspondence with the magnetic resonance waveform (40)
determining the states of the contrast agent in the volume element (50)
outputting information on the states of the contrast agent in the volume element (60).

Figure 2:
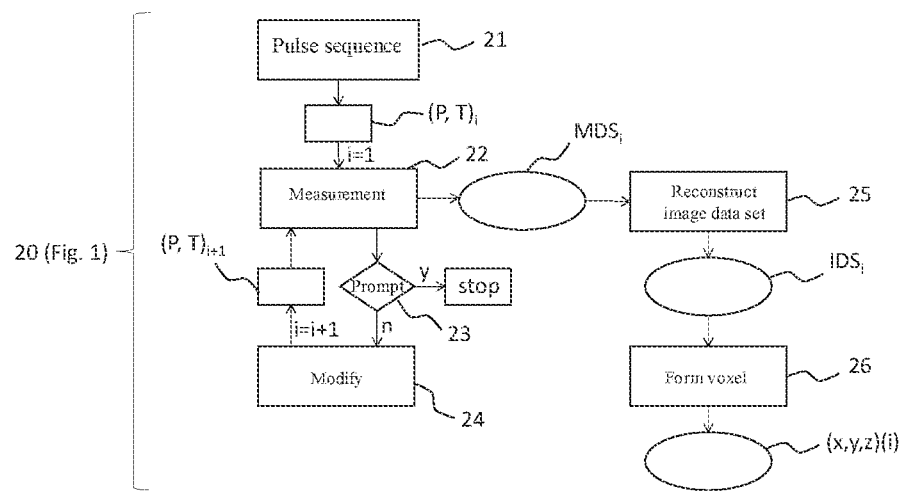
FIG. 2 shows an exemplary schematic representation of a preferred embodiment for the acquisition of a magnetic resonance waveform by means of a magnetic resonance fingerprinting method.

FIG. 2 shows an exemplary schematic representation of a preferred embodiment for the acquisition of a magnetic resonance waveform by means of a magnetic resonance fingerprinting method (Step 20 in FIG. 1).

A pulse sequence is chosen in the normal manner, for example in accordance with a desired contrast or other desired properties of the measured data that can be read with the pulse sequence (21).

The pulse sequence is executed with a first set (i=1) of acquisition parameters $P_i$, wherein measured data are to be scanned along a first k-space trajectory $T_i$ (P, T)$_i$. A k-space trajectory along which measured data are measured in a repetition can scan the k-space in a Cartesian, spiral or radial scan mode, or in a combination of said scan modes, or along a freely constructed trajectory.

In accordance with the pulse sequence, HF pulses are radiated into the examination region, gradients are switched, and the echo signals generated by the radiated HF pulses and the switched gradients are read (22). After excitation with a HF excitation pulse, measured data are acquired along the k-space trajectory $T_i$ and saved in a measured data set $MDS_i$.

Each measured data set $MDS_i$ is used to reconstruct an image data set $IDS_i$ (25); it is also possible to use only some of the measured data contained in the measured data set $MDS_i$ for the reconstruction. This results in one image data set $IDS_i$ per repetition i, i.e. a total of N image data sets $IDS_i$.

A prompt (23) asks the operator whether all N desired repetitions have been executed and the corresponding N measured data sets $MDS_i$ have been saved. If this is not the case ("n"), a k-space trajectory for the next repetition is selected and the parameters of the pulse sequence are appropriately modified and optionally additionally varied (24). A selected further k-space trajectory $T_{i+1}$ will generally differ from a previous k-space trajectory $T_i$.

With the next parameter $P_{i+1}$ obtained in this way and the selected further k-space trajectory $T_{i+1}$ ((P, T)$_{i+1}$), the pulse sequence is repeated and thus a new measurement (22) is performed, such that in successive repetitions data are measured along the selected k-space trajectories $T_i$, $T_{i+1}$. As regards the selection of trajectories, reference can be made to the extensive literature on magnetic resonance fingerprinting methods; an example is the published specification DE102016217675A1, the content of which is fully incorporated into this description by reference.

When all N desired repetitions have been executed and the corresponding N measured data sets $MDS_i$ have been saved ("y"), no further measurements are performed ("stop") and a voxel-time series (x,y,z)(i) is formed (26) for at least one voxel (x,y,z) in the reconstructed image data sets IDSthis being a reflection of signal intensity of the voxel (x,y,z) over the course of the acquisition times (and thus over the course of the successively executed repetitions (i) of the measured data sets MDS,). Such a voxel-time series (x,y,z) (i) is usually executed for all voxels (x,y,z) that lie within the examination region of interest. The voxel-time series (x,y, z)(i) formed are saved.

Figure 3:
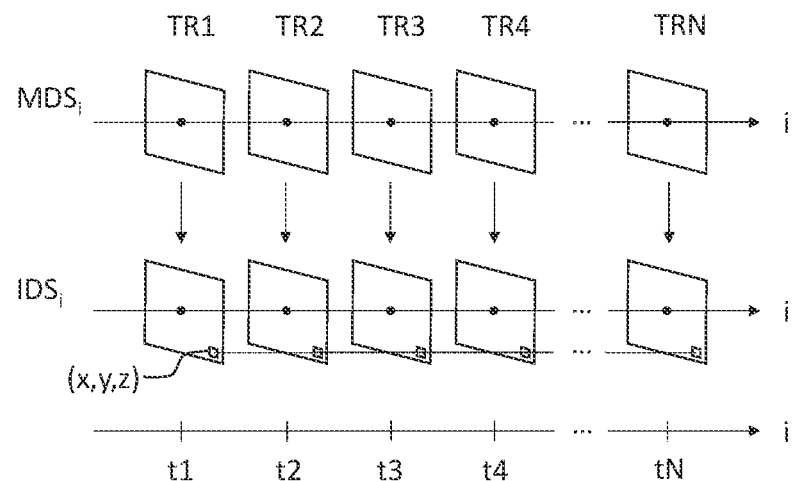
FIG. 3 shows an exemplary schematic representation of the relationship between measured data sets and image data sets over time, according to some embodiments.

FIG. 3 shows an exemplary schematic representation of the relationship between measured data sets $MDS_i$ and image data sets IDS, over time, i.e. over the course of i.

The top line shows the measured data sets $MDS_i$ in the order in which they were acquired in the repetitions TRi, the repetitions i=1, i=2, i=3, i=4, and i=N being explicitly shown by way of example. The second line shows in the same way the image data sets IDS, reconstructed from the measured data sets $MDS_i$, with a voxel (x,y,z) marked in the image data sets $IDS_i$ by way of example. Taking this voxel (x,y,z) by way of example, the respective intensity of the voxel (x,y,z) at the times T1 corresponding to the repetitions T1 can be plotted against time as a voxel-time series. A voxel-time series (x,y,z)(i) is a magnetic resonance waveform for a volume element of the examination region.

Figure 4:
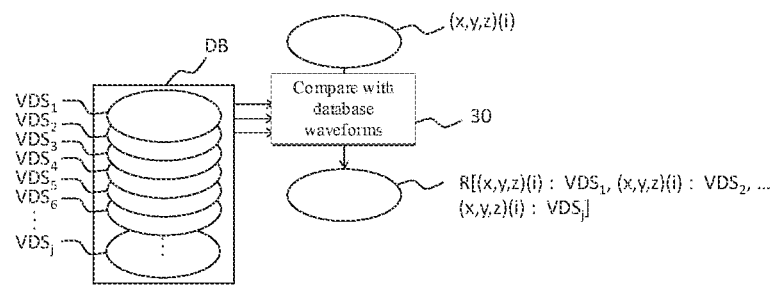
FIG. 4 shows an exemplary schematic representation of the comparison of magnetic resonance waveforms with database waveforms, according to some embodiments.

FIG. 4 shows an exemplary schematic representation of the comparison of magnetic resonance waveforms with database waveforms (Step 30 in FIG. 1).

Each saved voxel-time series (x,y,z)(i) from FIG. 2 is compared with a plurality of database waveforms $CDS_1$ to $CDS_j$ saved in a magnetic resonance fingerprinting database (DB) (30). The result of each comparison can be a similarity value R that indicates how similar a voxel-time series (x,y,z)(i) is to a database waveform.

Figure 5:
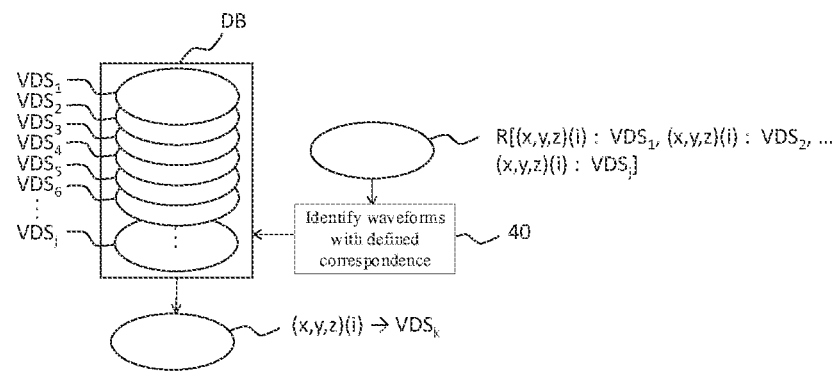
FIG. 5 shows an exemplary schematic representation of the identification of a database waveform having a defined correspondence with the magnetic resonance waveform, according to some embodiments.

FIG. 5 shows an exemplary schematic representation of the identification of a database waveform having a defined correspondence with the magnetic resonance waveform (Step 40 in FIG. 1).

Each voxel-time series (x,y,z)(i) is normally matched to a database waveform $CDS_k$, which is normally the database waveform that shows the greatest correspondence with the voxel-time series (x,y,z)(i) (maximum R value).

Figure 6:
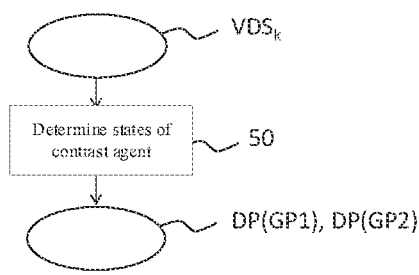
FIG. 6 shows an exemplary schematic representation of the determination of the states of the contrast agent for the volume element imaged in the respective voxel-time series, according to some embodiments.

FIG. 6 shows an exemplary schematic representation of the determination of the states of the contrast agent for the volume element imaged in the respective voxel-time series (x,y,z)(i) (Step 50 in FIG. 1). The states of the contrast agent are characterized by specific values of two tissue parameters TP1 and TP2. These values (database values) arise from the database waveform $CDS_k$ identified in Step 50. They are usually saved with the database waveform $CDS_k$ in the magnetic resonance fingerprinting database and can be read after $CDS_k$ has been identified.

Figure 7:
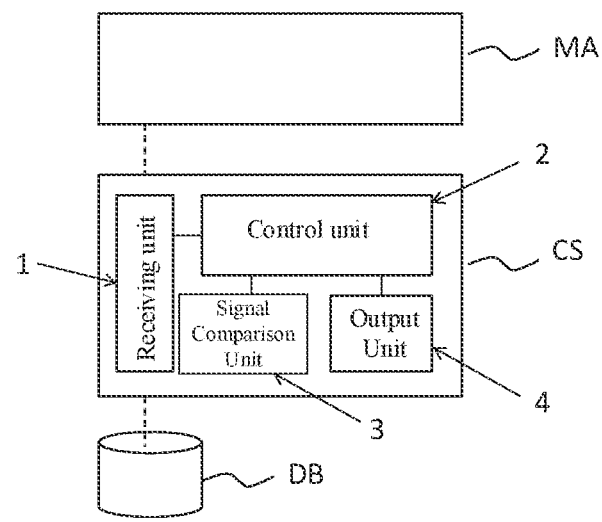
FIG. 7 shows an exemplary schematic representation of one embodiment of the system according to the invention.

FIG. 7 shows an exemplary schematic representation of one embodiment of the system according to the invention. The system comprises a receiving unit (1), a control unit (2), a signal comparison unit (3), and an output unit (4). The units mentioned are components of a computer system (CS). The receiving unit (1) is configured to receive magnetic resonance waveforms from a magnetic resonance system (MS) and database waveforms from a magnetic resonance fingerprinting database (DB). Reception can take place over a network (shown by dashed lines).

The invention claimed is:

1. A method comprising:
providing a magnetic resonance fingerprint database comprising a plurality of predicted magnetic resonance waveforms for a contrast agent in a first tissue type and a second tissue type, wherein the contrast agent has a first relaxation-shortening effect in the first tissue type and a second relaxation-shortening effect in the second tissue type;
administering the contact agent to an examination region;
using a magnetic resonance fingerprinting method, acquiring a magnetic resonance waveform for the contrast agent in a volume element of the examination region wherein the volume element of the examination region comprises the first tissue type and the second tissue type;
comparing the acquired magnetic resonance waveform with the plurality of predicted magnetic resonance waveforms in the magnetic resonance fingerprint database;
identifying a predicted waveform of the plurality of predicted magnetic resonance waveforms that corresponds with the acquired magnetic resonance waveform based on the comparison between the acquired magnetic resonance waveform with the plurality of predicted magnetic resonance waveforms;
determining a concentration of the contrast agent in the first tissue type and a concentration of the contrast agent in the second tissue type; and
outputting information associated with the concentration of contrast agent in the first tissue type and information associated with the concentration of the contrast agent in the second tissue type for the volume element.

2. The method of claim 1, wherein the contrast agent has a different molar relaxivity in the first tissue type than in the second tissue type.

3. The method of claim 2, wherein the molar relaxivity in the first tissue type is at least 1.5 times greater than in the second tissue type.

4. The method of claim 3, wherein the molar relaxivity at a magnetic field strength of a basic magnetic field of at least 1.5 tesla, preferably of at least 2 tesla, even more preferably of at least 2.5 tesla, even more preferably of at least 3 tesla, most preferably at a magnetic field strength of 0.4 tesla to at least 3 tesla, is in the first tissue type at least 1.5 times greater, preferably at least 2 times greater, even more preferably at least 2.5 times greater, than in the second tissue type.

5. The method of claim 2, wherein the molar relaxivity in the first tissue type is at least 2 times greater than in the second tissue type.

6. The method of claim 2, wherein the molar relaxivity in the first tissue type is at least at least 2.5 times greater than in the second tissue type.

7. The method of claim 1, wherein the contrast agent has a higher molar T1 relaxivity in the first tissue type than in the second tissue type.

8. The method of claim 1, wherein the contrast agent comprises gadoxetic acid or a salt of gadoxetic acid as contrast-enhancing active substance.

9. The method of claim 1, wherein the contrast agent comprises Gd-EOB-DTP disodium.

10. The method of claim 1, wherein hepatocytes are the first tissue type.

11. The method of claim 1, wherein healthy liver tissue is the first tissue type and diseased liver tissue is the second tissue type.

12. A system comprising
a receiving unit;
a signal comparison unit;
an output unit; and
a control unit configured to:
cause the receiving unit to receive a magnetic resonance waveform for a contrast agent in a volume element of an examination region, wherein the magnetic resonance waveform was generated using a magnetic fingerprinting method, and wherein the volume element of the examination region comprises a first tissue type and a second tissue type;
cause the receiving unit to receive, from a magnetic resonance fingerprint database, a plurality of predicted magnetic resonance waveforms for the contrast agent in the first tissue type and the second tissue type wherein the contrast agent has a first relaxation-shortening effect in the first tissue type and a second relaxation-shortening effect in the second tissue type;

cause the signal comparison unit to compare the magnetic resonance waveform for the contrast agent in the volume element of the examination region with the plurality of predicted magnetic resonance waveforms received from the magnetic resonance fingerprint database to identify a predicted waveform of the plurality of predicted magnetic resonance waveforms that corresponds with the magnetic resonance waveform generated for the contrast agent in the volume element and to determine a concentration of the contrast agent in the first tissue type and a concentration of the contrast agent in the second tissue type; and cause the output unit to save and/or output information associated with the concentration of contrast agent in the first tissue type and information associated with the concentration of the contrast agent in the second tissue type for the volume element.

13. A non-transitory computer readable medium storing one or more programs, the one or more programs comprising instructions, which when executed by a computer, cause the computer to:

receive a magnetic resonance waveform for a contrast agent in a volume element of an examination region, wherein the magnetic resonance waveform was acquired using a magnetic resonance fingerprinting method, and wherein the volume element of the examination region comprises a first tissue type and a second tissue type;

receive a plurality of predicted magnetic resonance waveforms for the contrast agent in the first tissue type and the second tissue type, wherein the contrast agent has a first relaxation-shortening effect in the first tissue type and a second relaxation-shortening effect in the second tissue type;

compare the magnetic resonance waveform for the contrast agent in the volume element of the examination region with the plurality of predicted magnetic resonance waveforms;

identify a predicted waveform of the plurality of predicted magnetic resonance waveforms that corresponds with the magnetic resonance waveform for the contrast agent in the volume element;

determine a concentration of the contrast agent in the first tissue type and a concentration of the contrast agent in the second tissue type; and output information information associated with the concentration of contrast agent in the first tissue type and information associated with the concentration of the contrast agent in the second tissue type for the volume element.

14. A magnetic resonance fingerprinting method, comprising using a contrast agent, wherein the contrast agent has different states in at least two different tissue types, for determining the different states in an imaged volume element.

15. The method of claim 14, wherein the contrast agent comprises gadoxetic acid or a salt of gadoxetic acid.

16. The method of claim 14, wherein hepatocytes are the first tissue type.

17. A magnetic resonance fingerprinting method, comprising using a contrast agent, wherein the contrast agent has different states in at least two different tissue types, the different states in an imaged volume element being recorded simultaneously in one measurement.

18. The method of claim 17, wherein the contrast agent comprises gadoxetic acid or a salt of gadoxetic acid.

19. The method of claim 17, wherein hepatocytes are the first tissue type.

* * * * *